(12) United States Patent
Edens

(10) Patent No.: US 6,391,041 B1
(45) Date of Patent: May 21, 2002

(54) RETRACTABLE OPHTHALMIC SURGICAL TOOL

(75) Inventor: Roger A. Edens, Oconomowoc, WI (US)

(73) Assignee: Escalon Medical Corporation, New Berlin, WI (US)

(\*) Notice: Subject to any disclaimer, the term of this patent is extended or adjusted under 35 U.S.C. 154(b) by 85 days.

(21) Appl. No.: 09/619,120

(22) Filed: Jul. 19, 2000

(51) Int. Cl.[7] .............................................. A61B 17/32
(52) U.S. Cl. ...................................... 606/167; 606/166
(58) Field of Search ................................ 606/166, 167, 606/170; 30/2, 151, 162, 164, 167, 286, 335

(56) References Cited

U.S. PATENT DOCUMENTS

| | | | | |
|---|---|---|---|---|
| 4,757,612 A | \* | 7/1988 | Peyrot ........................... | 30/151 |
| 5,330,492 A | \* | 7/1994 | Haugen ......................... | 30/151 |
| 5,391,177 A | \* | 2/1995 | Schwartz ..................... | 606/167 |
| 5,662,669 A | \* | 9/1997 | Abidin et al. ................ | 606/167 |
| 5,730,751 A | \* | 3/1998 | Dillon et al. ................. | 606/167 |
| 6,015,419 A | \* | 1/2000 | Strome et al. ............... | 606/167 |

\* cited by examiner

*Primary Examiner*—Eric F. Winakur
*Assistant Examiner*—Joseph A Cadugan
(74) *Attorney, Agent, or Firm*—Donald J. Ersler

(57) ABSTRACT

A retractable ophthalmic surgical tool includes a shell, slidable insert, slide button, spring, and blade. The shell is preferably a hollow tube. A first slot is formed through the wall of the shell at substantially a first end thereof. A second slot is formed through the wall of the shell at substantially a middle of the shell length. A connecting slot is formed between the first and second slots to enable the slide button to be slid therebetween. The slidable insert includes a body, a first cantilever arm, and a second cantilever arm. The blade is preferably inserted into a first end of the body. The first cantilever arm extends from substantially a middle of said body and the second cantilever arm extends from an end of the first cantilever arm. The slide button is attached to a top of the second cantilever arm at assembly. At least one side of the body has a groove formed therein to provide clearance for the spring. A hole is formed through a middle of the body for attachment of one end of the spring. An end plug is inserted into a second end of the shell for attachment of the other end of the spring.

15 Claims, 7 Drawing Sheets

RETRACTABLE OPHTHALMIC SURGICAL TOOL

BACKGROUND OF THE INVENTION

1. Field of the Invention

The present invention relates generally to surgical tools and more specifically to a retractable ophthalmic surgical tool for performing surgery on the eye.

2. Discussion of the Prior Art

Currently, there appears to be only two types of ophthalmic tools, scalpels, or lances. The first is a nonretractable type of ophthalmic scalpel. It is similar to a surgical scalpel used for making incisions in the body with the difference being the spear blade. The second type is a retractable ophthalmic lance which is described in U.S. Pat. No. 5,391,177 to Schwartz. The drawback to the Schwartz device is the inability of locking the lance in an extended position. The lack of locking feature makes its use inconvenient for a surgeon, because the surgeon must keep the lance extended and also manipulate the lance for surgery at the same time.

Accordingly, there is a clearly felt need in the art for a retractable ophthalmic surgical tool which allows the blade to be securely locked in an extended position, yet protects the handlers thereof from being cut by the blade.

SUMMARY OF THE INVENTION

The present invention provides a retractable ophthalmic surgical tool which requires a deliberate action to release the blade from an extended position. The retractable ophthalmic surgical tool includes a shell, slidable insert, slide button, spring, and blade. The shell is preferably a hollow tube which comes to a decreasing taper at a first end thereof. A first slot is formed through the wall of the shell at substantially a first end thereof. A second slot is formed through the wall of the shell at substantially a middle of the shell length. A connecting slot is formed through the wall of the shell and enables the slide button to slide between the first and second slots.

The slidable insert includes a body, a first cantilever arm, and a second cantilever arm. A first end of the body is tapered to fit inside the first end of the shell. The blade is retained in the first end of the body. The first cantilever arm extends from substantially a middle of the body and the second cantilever arm extends from an end of the first cantilever arm. The slide button is attached to a top of the second cantilever arm at assembly. At least one side of the body has a groove formed therein to provide clearance for the spring. A hole is formed through a middle of the body for attachment of one end of the spring. An end plug is inserted into a second end of the shell. An end of the end plug has a hole formed therethrough for attachment of the other end of the spring.

Accordingly, it is an object of the present invention to provide a retractable ophthalmic surgical tool which securely locks the blade in an extended position.

Finally, it is another object of the present invention to provide a retractable ophthalmic surgical tool which prevents a cutting injury to a handler thereof.

These and additional objects, advantages, features and benefits of the present invention will become apparent from the following specification.

DETAILED DESCRIPTION OF THE PREFERRED EMBODIMENTS

Figure 1:
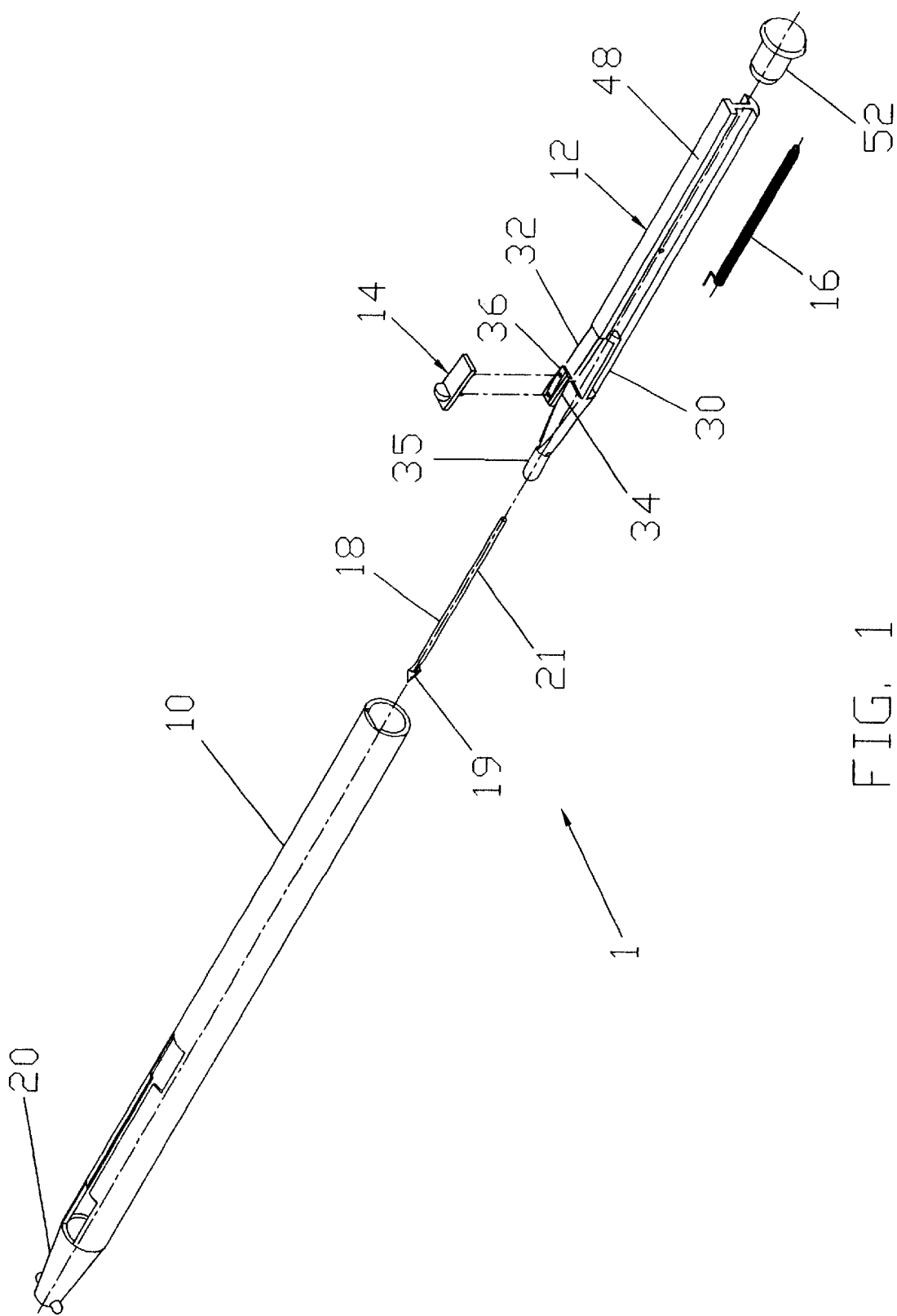
FIG. 1 is an exploded perspective view of a retractable ophthalmic surgical tool in accordance with the present invention.
Figure 2:
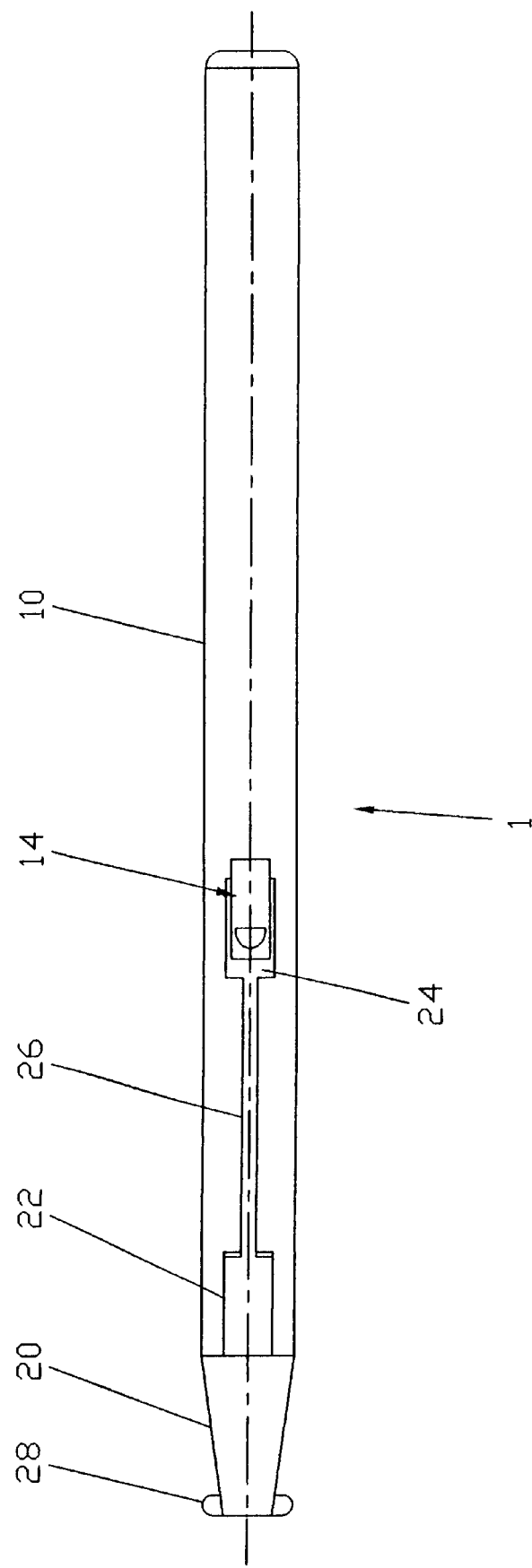
FIG. 2 is a top view of a retractable ophthalmic surgical tool with the blade in a retracted position in accordance with the present invention.
Figure 3:
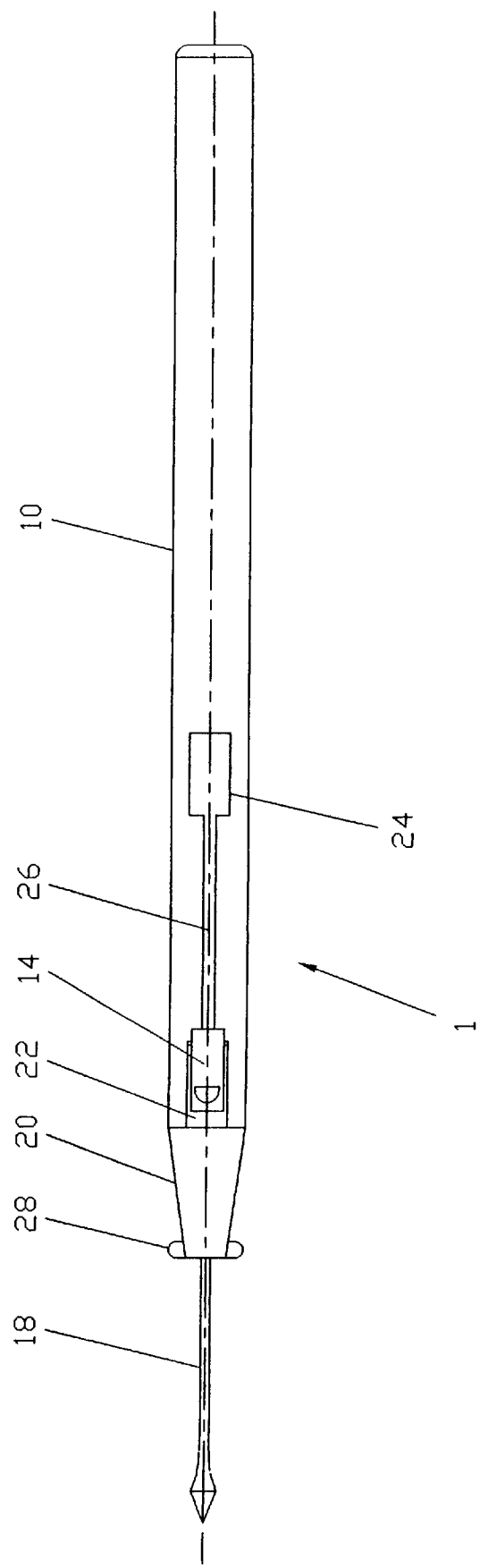
FIG. 3 is a top view of a retractable ophthalmic surgical tool with the blade in an extended position in accordance with the present invention.
Figure 4:
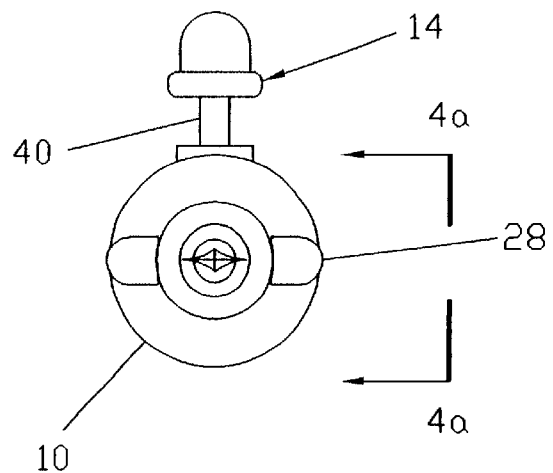
FIG. 4 is an enlarged front end view of a retractable ophthalmic surgical tool in accordance with the present invention.
Figure 4A:
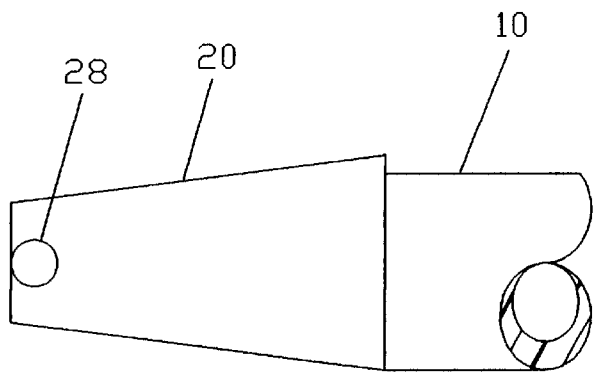
FIG. 4a is an enlarged partial side view of a front of a retractable ophthalmic surgical tool in accordance with the present invention.
Figure 5:
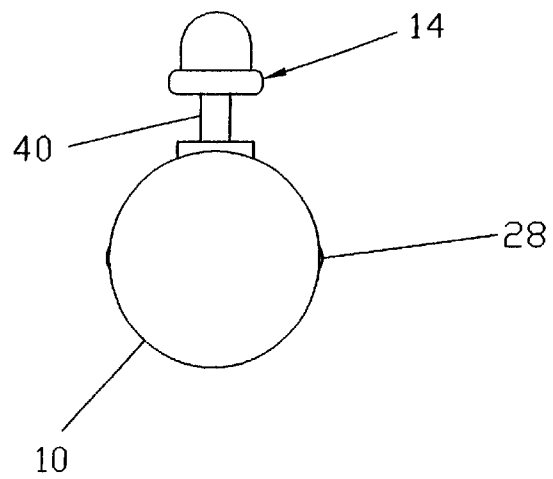
FIG. 5 is an enlarged rear end view of a retractable ophthalmic surgical tool in accordance with the present invention.

With reference now to the drawings, and particularly to FIG. 1, there is shown an exploded perspective view of a retractable ophthalmic surgical tool 1. With reference to FIGS. 2–5, the retractable ophthalmic surgical tool 1 includes a shell 10, slidable insert 12, slide button 14, spring 16, and blade 18. The shell 10 is preferably a hollow tube. The shape of the shell 10 should not be limited to a round shape, but could also be square or any other shape. The inner diameter could also be a square or any other shaped lengthwise opening. A decreasing taper 20 is preferably formed on a first end of the shell 10. An outer periphery of the slidable insert 12 is slidable along the length of the inner diameter of the shell 10. A first slot 22 is formed through a top of the shell 10 at substantially a first end thereof. A second slot 24 is formed through the top of the shell 10 at substantially a middle of the axial length of the shell. A connecting slot 26 is formed through the wall of the shell 10 between the first and second slots, such that the slide button 14 may slide between the first and second slots. A pair of opposing projections 28 preferably extend outward from a front of the decreasing taper 20. Each edge of the blade 18 is aligned with each of the opposing projections 28.

Figure 6:
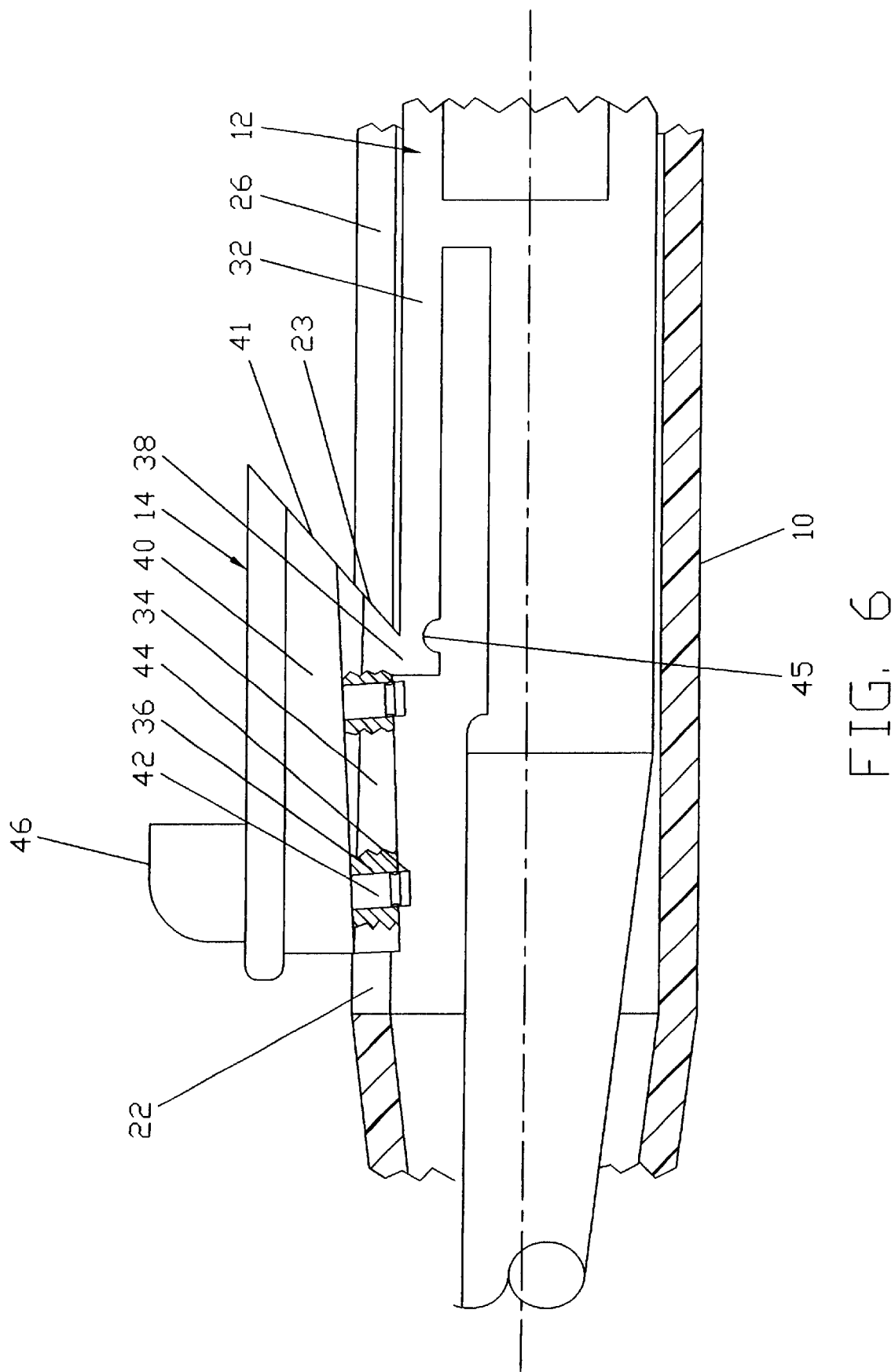
FIG. 6 is an enlarged cross sectional side view of a slide button of a retractable ophthalmic surgical tool locked in a first slot in accordance with the present invention.
Figure 7:
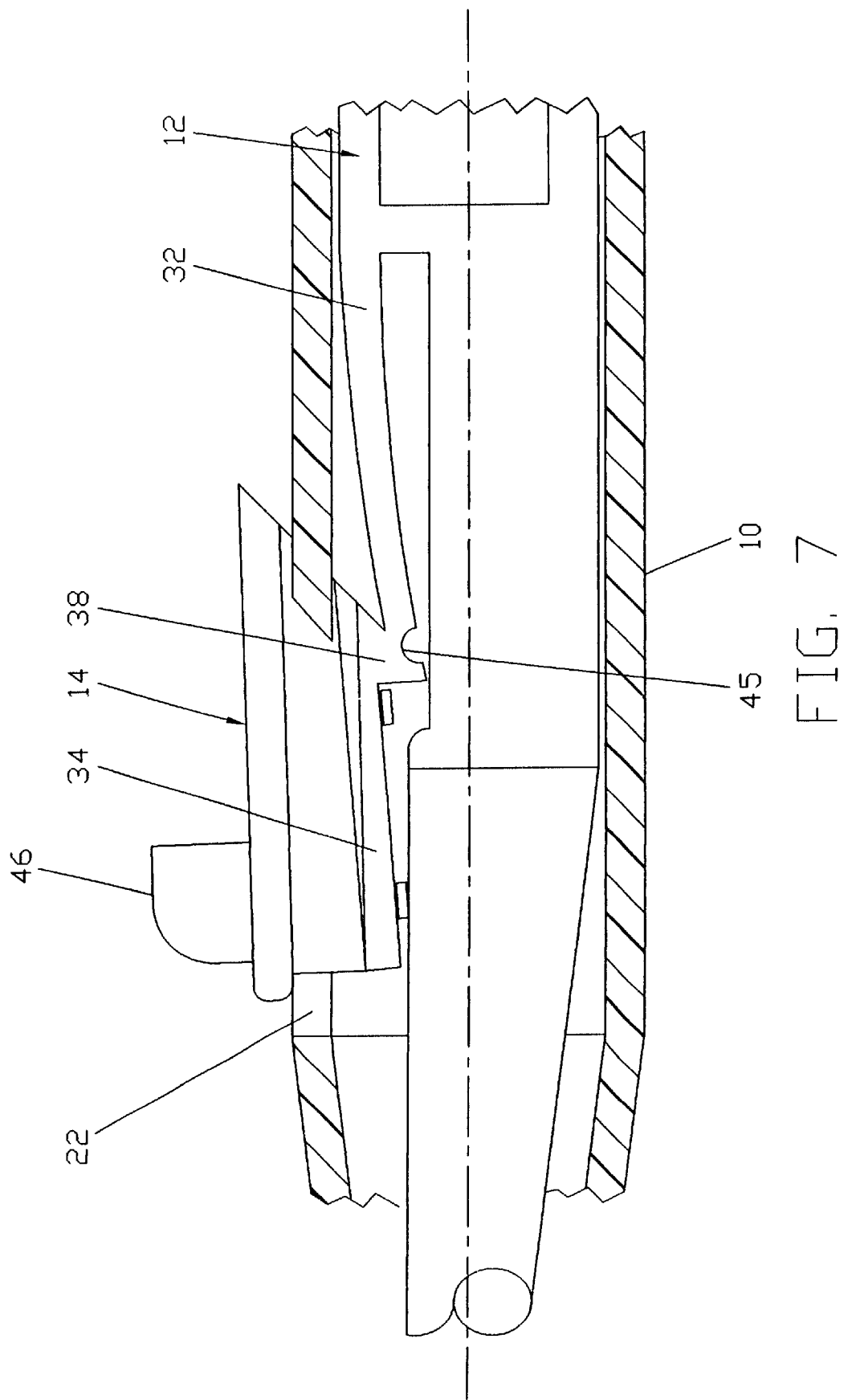
FIG. 7 is an enlarged cross sectional side view of a slide button of a retractable ophthalmic surgical tool unlocked in a first slot in accordance with the present invention.

With reference to FIGS. 6–7, the slidable insert 12 includes a body 30, a first cantilever arm 32, and a second cantilever arm 34. A cutting edge 19 is formed on a first end of the blade 18 and a shank 21 is formed on a second end of the blade 18. A first end of the body 30 has a blade diameter 35 which is sized to securely retain the shank 21 of the blade 18 and to fit inside the decreasing taper 20 of the shell 10. A blade hole is preferably formed in the blade diameter 35 for insertion of the shank 21. Preferably, a press fit is formed between the outer diameter of the blade 18 and the blade hole. The blade 18 could also be molded inside the blade hole, or attached through any other appropriate assembly method such as sonic welding, application of adhesive, or threads.

The first cantilever arm 32 extends from substantially a middle of the body 30 and the second cantilever arm 34 extends from an end of the first cantilever arm 32. The junction 38 between the first cantilever arm 32 and the second cantilever arm 34 must be more flexible than the first cantilever arm 32 to allow the button 14 to be disengaged from the first slot 22. A cutout 45 is preferably formed adjacent the junction 38 to allow the flexibility thereof to be changed by reducing the size of the cutout 45.

The button 14 includes relieved sides 40, a pair of locking pins 42, and a finger projection 46. The relieved sides 40 are sized to slidably fit in the connecting slot 26. The pair of locking pins 42 fit in a pair of holes 36 formed in the second cantilever member 34. An enlarged head 44 at the end of each locking pin 42 ensures that the button 14 remains secured to the second cantilever arm 34.

The second end 23 of the first slot 22 must be angled toward a second end of the shell 10 to prevent accidental disengagement of the button 14 from the first slot 22. A rear of the junction 38 and a second end 41 of the button 14 must also be angled toward a second end of the shell 10 to match the second end 23 of the first slot 22.

Extending the blade 18 requires a front of the button 14 to be pushed down (depressed) and forward until a second end 41 of the button 14 clears the second end 23 of the first slot 22. Thumb or finger pressure on the button 14 is then released and the blade 18 is securely extended; since the first cantilever arm 32 is less flexible than the junction 38, the second end 41 of the button 14 will lock into the second end 23 of the first slot 22, before forward pressure on the button 14 is released; thus enabling the button 14 to be latched, before the spring 16 retracts. The finger projection 46 is preferably used to slide the button 14. Releasing the button 14 from the first slot 22 requires that the button 14 be pushed forward and then down. The angled areas of the first slot 22, junction 38, and second end 41 make it necessary to push the button 14 forward to release the blade 18 from the extended position and thus ensure that the blade 18 is secure while in the extended position. The slidable insert 12 will slide back to the second slot 24 and the button 14 will automatically lock itself in the second slot 24.

Figure 8:
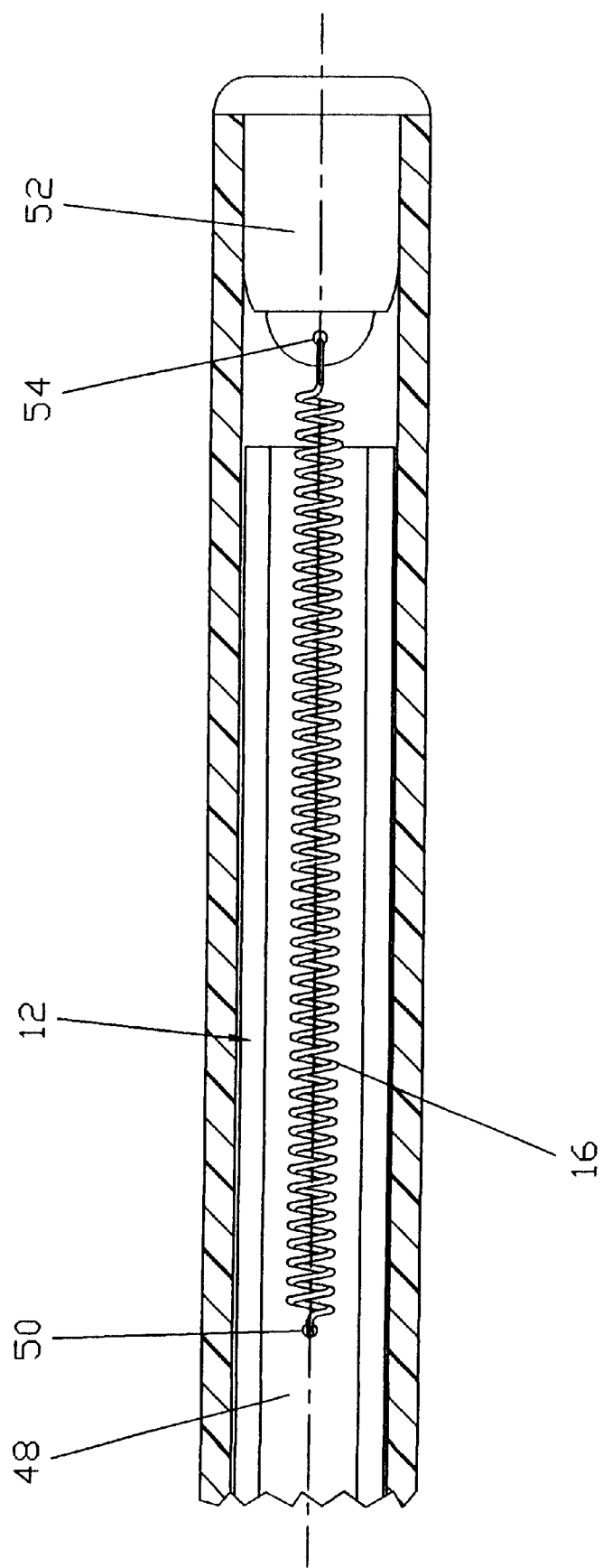
FIG. 8 is a side cross sectional view of a spring pulling a slidable insert of a retractable ophthalmic surgical tool in accordance with the present invention.

FIG. 8 discloses the spring 16 pulling the slidable insert 12 backward toward the second end of the shell 10. At least one groove 48 is formed along a second end of the slidable insert 12 to provide clearance for the spring 16. The spring 16 is preferably an extension spring. A spring hole 50 is formed through a middle of the body 30 for attachment of one end of the spring 16. An end plug 52 is inserted into a second end of the shell 10. An end of the end plug has a hole 54 formed therethrough for attachment of the other end of the spring 16. The spring 16 retains the blade 18 in a retracted position and automatically retracts the blade 18 from the extended position when the button 14 is released from the first slot 22. The spring 16 also pulls the button 14 backwards to secure the blade 18 in the extended position.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. A retractable ophthalmic surgical tool comprising:
   a shell having a lengthwise opening, a first end, and a second end, a first slot being formed through substantially a first end, a second slot being formed though substantially a middle of said shell, a connecting slot providing a connection between said first and second slots;
   a slidable insert having an outer periphery, a first end, and a second end, a cantilever arm extending from substantially a middle of said slidable insert, a second cantilever arm extending from an end of said cantilever arm, a junction between said cantilever arm and said second cantilever arm being more flexible than said cantilever arm;
   a blade extending from said first end of said slidable insert; and
   a button extending from said second cantilever arm, wherein depression and forward movement of said button from said second slot to said first slot placing said blade in an extended position.

2. The retractable ophthalmic surgical tool of claim 1, further comprising:
   an extension spring being attached to said second end of said slidable insert and a second end of said shell, said extension spring pulling said slidable insert toward said second end of said shell.

3. The retractable ophthalmic surgical tool of claim 1 wherein:
   a second end of said first slot being angled toward said second end of said shell, a rear of said junction, and a second end of said button being angled toward said second end of said shell.

4. The retractable ophthalmic surgical tool of claim 1 wherein:
   a decreasing taper being formed on a first end of said shell.

5. The retractable ophthalmic surgical tool of claim 4, further comprising:
   a pair of opposing projections extending outward from a front of said decreasing taper.

6. A retractable ophthalmic surgical tool comprising:
   a shell having a lengthwise opening, a first end, and a second end, a first slot being formed through substantially a first end, a second slot being formed though substantially a middle of said shell, a connecting slot providing a connection between said first and second slots;
   a slidable insert having an outer periphery, a first end, and a second end, a first cantilever arm extending from substantially a middle of said slidable insert, a second cantilever arm extending from an end of said first cantilever arm;
   a blade extending from said first end of said slidable insert; and
   a button extending from said second cantilever arm, depression and forward movement of said button from said second slot to said first slot placing said blade in an extended position.

7. The retractable ophthalmic surgical tool of claim 6, further comprising:
   an extension spring being attached to said second end of said slidable insert and a second end of said shell, said extension pulling said slidable insert toward said second end of said shell.

8. The retractable ophthalmic surgical tool of claim 7, wherein:
   a junction between said first and said second cantilever arms being more flexible than said first cantilever arm.

9. The retractable ophthalmic surgical tool of claim 6 wherein:
   a second end of said first slot being angled toward said second end of said shell, a rear of said junction, and a second end of said button being angled toward said second end of said shell.

10. The retractable ophthalmic surgical tool of claim 6 wherein:

a decreasing taper being formed on a first end of said shell.

11. The retractable ophthalmic surgical tool of claim 10, further comprising:

a pair of opposing projections extending outward from a front of said decreasing taper.

12. A retractable ophthalmic surgical tool comprising:

a shell having an inner diameter, a first end, and a second end, a first slot being formed through substantially a first end, a second slot being formed though substantially a middle of said shell, a connecting slot providing a connection between said first and second slots;

a slidable insert having an outer periphery, a first end, and a second end, a first cantilever arm extending from substantially a middle of said slidable insert, a second cantilever arm extending from an end of said first cantilever arm;

a blade extending from said first end of said slidable insert;

a button extending from said second cantilever arm, depression and forward movement of said button from said second slot to said first slot placing said blade in an extended position; and an extension spring being attached to said second end of said slidable insert and a second end of said shell, said extension pulling said slidable insert toward said second end of said shell; and a junction between said first and second cantilever arms being more flexible than said first cantilever arm.

13. The retractable ophthalmic surgical tool of claim 12 wherein:

a second end of said first slot being angled toward said second end of said shell, a rear of said junction, and a second end of said button being angled toward said second end of said shell.

14. The retractable ophthalmic surgical tool of claim 12 wherein:

a decreasing taper being formed on a first end of said shell.

15. The retractable ophthalmic surgical tool of claim 14, further comprising:

a pair of opposing projections extending outward from a front of said decreasing taper.

* * * * *